(12) United States Patent
Meno

(10) Patent No.: US 9,758,746 B2
(45) Date of Patent: Sep. 12, 2017

(54) CLEANSING COMPOSITION FOR PUMP FOAMER COMPRISING SOAP AND PROPYLENE GLYCOL

(71) Applicant: SHISEIDO COMPANY, LTD., Chuo-ku, Tokyo (JP)

(72) Inventor: Takashi Meno, Yokohama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 0 days.

(21) Appl. No.: 14/785,035

(22) PCT Filed: Mar. 14, 2014

(86) PCT No.: PCT/JP2014/056841
§ 371 (c)(1),
(2) Date: Oct. 16, 2015

(87) PCT Pub. No.: WO2014/171238
PCT Pub. Date: Oct. 23, 2014

(65) Prior Publication Data
US 2016/0075974 A1 Mar. 17, 2016

(30) Foreign Application Priority Data

Apr. 18, 2013 (JP) ................................ 2013-087195

(51) Int. Cl.
| | | |
|---|---|---|
| A61Q 5/02 | (2006.01) |
| C11D 1/02 | (2006.01) |
| C11D 1/04 | (2006.01) |
| C11D 1/83 | (2006.01) |
| C11D 3/32 | (2006.01) |
| C11D 17/08 | (2006.01) |
| C11D 3/20 | (2006.01) |
| A61Q 19/10 | (2006.01) |
| A61K 8/34 | (2006.01) |
| A61K 8/36 | (2006.01) |
| C11D 9/26 | (2006.01) |
| C11D 10/04 | (2006.01) |
| C11D 1/52 | (2006.01) |

(52) U.S. Cl.
CPC ............ *C11D 3/2065* (2013.01); *A61K 8/345* (2013.01); *A61K 8/361* (2013.01); *A61Q 5/02* (2013.01); *A61Q 19/10* (2013.01); *C11D 3/2048* (2013.01); *C11D 9/26* (2013.01); *C11D 10/047* (2013.01); *C11D 17/08* (2013.01); *A61K 2800/87* (2013.01); *C11D 1/523* (2013.01)

(58) Field of Classification Search
CPC .... A61Q 5/02; C11D 1/02; C11D 1/04; C11D 1/83; C11D 3/0094; C11D 3/2041; C11D 3/32; C11D 7/3263; C11D 7/5004; C11D 9/265; C11D 17/08
See application file for complete search history.

(56) References Cited

U.S. PATENT DOCUMENTS

| | | | | |
|---|---|---|---|---|
| 2011/0039745 A1* | 2/2011 | Hermanson | ............ | A61K 8/361 510/159 |
| 2011/0039746 A1* | 2/2011 | Hermanson | ............ | A61K 8/361 510/159 |
| 2012/0309660 A1* | 12/2012 | Kawasoe | ................. | A61K 8/73 510/119 |

FOREIGN PATENT DOCUMENTS

| | | | |
|---|---|---|---|
| CN | 102470083 | * | 7/2010 |
| CN | 102470083 | | 5/2012 |
| JP | 2006-183039 | | 7/2006 |
| JP | 2006183039 | | 7/2006 |
| JP | 2006-342293 | | 12/2006 |
| JP | 2006342293 | | 12/2006 |
| JP | 2007-091968 | | 4/2007 |
| JP | 2007091968 | | 4/2007 |
| JP | 2010-059247 | | 3/2010 |
| JP | 2010059247 | | 3/2010 |
| JP | 2011-012034 | | 1/2011 |
| JP | 2011012034 | | 1/2011 |
| JP | 2013-087195 | | 9/2013 |
| SG | 176871 | | 1/2012 |

OTHER PUBLICATIONS

PCT/JP2014/056841 International Search Report mailed Apr. 28, 2014 2 pages—English, 3 pages-13 Japanese.
JP 2013-087195, Decision to Grant a Patent dated Aug. 22, 2013, 3 pages—English, 3 pages—Japanese.
JP 2013-087195, Notification of Reasons for Refusal dated Jun. 21, 2013, 3 pages—English, 3 pages—Japanese.
JP 2013-087195, Remarks and Amendments dated Aug. 9, 2013, 7 pages—English, 7 pages—Japanese.
PCT/JP2014/056841, International Search Report mailed Apr. 28, 2014, 2 pages—English, 2 pages—Japanese.
Chinese Appln. No. 201480021940.7, Office Action dated Mar. 29, 2016, 5 pages—English, 10 pages—Chinese.

* cited by examiner

*Primary Examiner* — Charles Boyer
(74) *Attorney, Agent, or Firm* — Andrew F. Young, Esq.; Lackenbach Siegel, LLP

(57) ABSTRACT

The present invention provides a cleansing composition for a pump foamer that not only has excellent foam quality and low-temperature stability, but can also be easily rinsed away with a small amount of water. A cleansing composition to be dispensed by a pump foamer of the present invention is characterized by comprising: (a) 2 to 5 mass % of an ionic surfactant; and (b) 20 to 60 mass % of a polyhydric alcohol comprising propylene glycol; wherein at least 90 mass % of the (a) ionic surfactant is accounted for by a higher fatty acid soap having 5 to 25 carbon atoms, and an amount of propylene glycol contained in the (b) polyhydric alcohol is less than 20 mass % with respect to the entire composition.

9 Claims, No Drawings

CLEANSING COMPOSITION FOR PUMP FOAMER COMPRISING SOAP AND PROPYLENE GLYCOL

CROSS REFERENCE TO RELATED APPLICATIONS

This application relates to and claims priority as a 371 national-phase from PCT/JP2014/056841 filed Mar. 14, 2014, the entire contents of which are incorporated herein by reference, which claims priority from JP Ser. No.:2013-087195 filed on Apr. 18, 2015.

FIGURE SELECTED FOR PUBLICATION

None

TECHNICAL FIELD

The present invention relates to a cleansing composition that is contained in a non-gas type foam-dispensing container having a porous membrane such as a pump foamer, and dispensed as foam through the aforementioned porous membrane at the time of use. More specifically, the invention relates to a cleansing composition for a pump foamer excelling in foaming ability and foam quality, while also having excellent rinsability.

BACKGROUND ART

Liquid cleansing compositions that are contained in non-gas type foam dispensing containers such as pump foamers and dispensed from the container as foam at the time of use are known. This type of cleansing composition is mixed with air when passing through a porous membrane provided in the container to be dispensed as foam, and various improvements have been made in order to obtain a creamy foam quality and prevent clogging of the porous membrane.

For example, Patent Document 1 describes that a blend of (a) a short-chain acyl taurine salt, (b) an amphoteric surfactant, and (c) a cationized starch does not clog the container, stably provides a creamy foam quality even at low temperatures, and also has conditioning effects. However, the cleansing composition of Patent Document 1 does not contain a higher fatty acid salt as an anionic surfactant.

On the other hand, when including a higher fatty acid salt as an anionic surfactant, at least 5 wt %, preferably at least 8 wt % of the surfactant is conventionally added in order to obtain a fine, creamy foam quality. However, particularly when adding a long-chain higher fatty acid salt with more than 12 carbon atoms, there was a problem in that precipitation would occur at low temperatures.

Patent Document 2 describes that by using an alkanolamine salt as the higher fatty acid salt, and adding it in combination with a polyoxyethylene alkyl phosphoric acid ester salt, 1 to 7 wt % of a monohydric alcohol, and 3 to 20 wt % of a polyhydric alcohol, a fine foam quality and excellent foam retention are achieved.

Patent Document 3 describes a cleansing composition wherein the number of carbon atoms in the alkyl group in the higher fatty acid salt is adjusted to a specific proportion, and it is combined with an amphoteric or semi-polar surfactant and a compound having an acid dissociation constant of 8.0 to 11.0 (specifically an amine compound such as monoethanolamine), capable of suppressing the generation of precipitates even when the pH of the cleansing composition decreases over time, thereby preventing dogging of pump foamer containers.

However, conventional pump foamer cleansers such as those described in Patent Documents 2 and 3 tend to place importance on improvement of foam quality, and even if they have improved low-temperature stability, they still have the problem of inadequate rinsability.

RELATED ART

Patent Documents

Patent Document 1: JP 2009-292969 A
Patent Document 2: JP H5-132700 A
Patent Document 3: JP 5071687 B

SUMMARY OF THE INVENTION

Problems to be Solved by the Invention

The present invention was made in consideration of the above-described circumstances of the conventional art, and has the purpose of offering a cleansing composition for a pump foamer that not only has excellent foam quality and low-temperature stability, but can also be easily rinsed away with a small amount of water.

Means for Solving the Problems

As a result of performing diligent research in order to solve the above-described problems, the present inventors discovered that a cleansing composition that not only has a rich foam quality and does not cause clogging even at low temperatures, but also has exceptional rinsability, can be obtained by suppressing the amount of ionic surfactant of which the majority is accounted for by a higher fatty acid soap, and adding a predetermined amount of a polyhydric alcohol comprising propylene glycol, thereby achieving the present invention.

In other words, the present invention offers a cleansing composition to be discharged from a pump foamer, comprising:
(a) 2 to 5 mass % of an ionic surfactant; and
(b) 20 to 60 mass % of a polyhydric alcohol comprising propylene glycol;
wherein at least 90 mass % of the (a) ionic surfactant is accounted for by a soap of a higher fatty acid having 5 to 25 carbon atoms, and an amount of propylene glycol contained in the (b) polyhydric alcohol is less than 20 mass % with respect to the entire composition.

EFFECTS OF THE INVENTION

The cleansing composition of the present invention has a rich foam quality, excels in low-temperature stability, and has exceptional rinsability in being capable of being easily rinsed away with a small amount of water.

MODES FOR CARRYING OUT THE INVENTION

Herebelow, the present invention will be explained in detail.
(a) Ionic Surfactant
The ionic surfactant used in the present invention consists of one or more chosen from among anionic surfactants, cationic surfactants and amphoteric surfactants.

Examples of anionic surfactants include those of carboxylate type such as fatty acid soaps, N-acyl glutamates and alkyl ether acetates, those of sulfonic acid type such as α-olefin sulfonates, alkane sulfonates and alkylbenzene sulfonic acids; those of sulfate type such as higher alcohol sulfates, and those of phosphate type.

The cleansing composition of the present invention is characterized in that, as anionic surfactants, higher fatty acid soaps account for 90 mass % or more of the ionic surfactant (ingredient a).

Higher fatty acid soaps consist of salts of higher fatty acid anions having a linear or branched saturated or unsaturated monovalent hydrocarbon group with approximately 5 to 25 carbon atoms bonded to a carboxyl group, and counter-cations thereof, wherein the hydrocarbon group may optionally be partially substituted by a hydroxyl group or the like.

Specific examples of fatty acids capable of forming higher fatty acid soaps include caproic acid, heptanoic acid, caprylic acid, pelargonic acid, capric acid, undecanoic acid, lauric acid, caproleic acid, undecylenic acid, lauroleic acid, 2-ethylbutanoic acid, isopentanoic acid, 2-ethylpentanoic acid, 2-ethylhexanoic acid, isononanoic acid, 3,5,5-trimethylhexanoic acid, tridecanoic acid, tetramethylnonanoic acid, myristic acid, pentadecanoic acid, palmitic acid, stearic acid, arachic acid, behenic acid, lignoceric acid, cerotic acid, myristoleic acid, palmitoleic acid, oleic acid, elaidic acid, gondoic acid, erucic acid, selacholeic acid, linoleic acid, linoelaidic acid, linolenic acid, arachidonic acid, 2-hexyldecanoic acid, isostearic acid, 12-hydroxystearic acid, coconut oil fatty acid, hydrogenated coconut oil fatty acid, palm oil fatty acid, hydrogenated palm oil fatty acid, palm kernel oil fatty acid, hydrogenated palm kernel oil fatty acid, beef tallow fatty acid and hydrogenated beef tallow fatty acid.

Among these specific examples, one or a combination of two or three types chosen from among lauric acid, myristic acid and palmitic acid is preferably used. In particular, when using a combination of all three of lauric acid, myristic acid and palmitic acid, the lauric acid content should preferably be greater than the content of other fatty acids in view of the low-temperature stability.

While the counter-cation for neutralizing the higher fatty acid anion is not particularly limited, alkali metal cations, particularly potassium cations, are preferred.

Examples of cationic surfactants include aliphatic amine salts, alkyl quaternary ammonium salts, aromatic quaternary ammonium salts, pyridinium salts and imidazolinium salts.

Examples of amphoteric surfactants include carbobetaine type amphoteric surfactants such as alkylbetaines and alkylamidobetaines, sulfobetaine type amphoteric surfactants such as alkylsulfobetaines and alkylhydroxysulfobetaines, phosphobetaine type amphoteric surfactants, innidazoline type amphoteric surfactants, and amidoamino acid salts.

Examples of alkylbetaines include lauryl dimethylaminoacetic acid betaine and the like. Examples of alkylamidobetaines include coconut oil fatty acid amidopropyl betaine and the like. Examples of alkylsulfobetaines include coconut oil fatty acid dimethylsulfopropyl betaine and the like. Examples of alkylhydroxysulfobetaines include lauryl dimethylaminohydroxysulfobetaine and the like. Examples of phosphobetaine-type amphoteric surfactants include lauryl hydroxyphosphobetaine and the like. Examples of imidazoline-type amphoteric surfactants include coconut oil alkyl-N-hydroxyethyl imidazolinium betaine.

The ionic surfactant (ingredient a) content in the cleansing composition of the present invention is 2 to 5 mass %. If the content is less than 2 mass %, the foaming ability will not be sufficient, and if more than 5 mass % is added, then the rinsability will become insufficient. The upper limit of the content may, for example, be set at 4.5 mass % or 4.0 mass %. The present invention was able to greatly improve the rinsability of the cleaning composition discharged from a pump foamer, while maintaining good foam quality by suppressing the amount of ionic surfactant compared to conventional cleansers discharged from pump foamers, while also setting the proportion accounted for by a higher fatty acid soap therein to at least the predetermined value (90 mass %) described above.

(b) Polyhydric Alcohol

The polyhydric alcohol blended in the cleansing composition of the present invention may be chosen from among those normally contained in cosmetics or the like, and is not particularly limited, but examples include glycerin, propylene glycol, dipropylene glycol, 1,3-butylene glycol, ethylene glycol and sorbitol.

Among the above-described polyhydric alcohols, propylene glycol is preferable since its addition improves the low-temperature stability, and the polyhydric alcohol in the present invention contains propylene glycol as an essential ingredient. However, the upper limit of the propylene glycol content should be less than 20 mass %, preferably less than 15 mass %, and more preferably less than 12 mass % with respect to the entire composition. On the other hand, while the lower limit of the propylene glycol content is not particularly limited, it should preferably be at least 1 mass %, more preferably at least 3 mass %, and even more preferably at least 5 mass % with respect to the entire composition. Additionally, sorbitol should preferably be added since it improves the resulting foam quality.

The polyhydric alcohol (ingredient b) content in the cleansing composition of the present invention should be 20 to 60 mass %, preferably 25 to 55 mass %, and more preferably 30 to 50 mass %. If the amount is less than 20 mass %, then clogging may occur in the porous membrane of the pump former, and if added in excess of 60 mass %, the foam quality tends to drop.

The low-temperature stability of the cleansing composition of the present invention can be further improved by adding a small amount of a non-ionic surfactant. Specific examples of non-ionic surfactants that are particularly effective in the present invention include coconut oil fatty acid diethanolamide (1:1 type, 1:2 type) and polyglyceryl-4 lauryl ether.

When adding a non-ionic surfactant, the content should be 3 mass % or less, preferably 1 mass % or less, and more preferably 0.8 mass % or less.

There are no particular limitations on other blendable ingredients as long as they are normally used in liquid cleansing compositions. Specific examples include oils, silicones, lower or higher alcohols, lanolin derivatives, protein derivatives, various medicaments, sterilizers, preservatives, pH adjusters, antioxidants, metal ion sequestering agents, chelating agents, UV absorbing agents, plant and animal extracts or derivatives thereof, colorants, fragrances, pigments, organic or inorganic powders, and clay minerals. One or more of these may be chosen as needed and added. However, the amounts thereof must be in a range not interfering with the characteristics of the present invention which are a foam that is stable and rich even at low temperatures and exceptional rinsability.

For example, the cleanser of the present invention only contains a limited amount of non-ionic surfactant, so in order to achieve emulsion stability, the amount of oil added should preferably be low. While not particularly limited, the oil content in the cleansing composition of the present invention should preferably be less than 1 mass %, more preferably less than 0.8 mass %, and even more preferably less than 0.5 mass %.

The cleansing composition of the present invention, while not thus limited, can be offered as a low-viscosity liquid having a viscosity, for example, of 30 mPa·s or less, preferably about 10 mPa·s as measured by a Brookfield type rotary viscometer at a temperature of 0 to 50° C.

The cleansing composition of the present invention can be produced according to conventional methods using the essential ingredients and optional ingredients described above.

The cleansing composition of the present invention, upon being prepared, is loaded into a non-gas type foam dispensing container having a porous membrane. The non-gas type foam dispensing container used in the present invention may be of any type that is publicly known as long as it is of a type that mixes a predetermined amount of liquid cleansing composition with a predetermined amount of air and dispenses them from the container in the form of a foam at the time of use. Specific examples include squeeze foamers that are used by pressing the trunk portion of a soft container with the fingers and pump foamers that are used by pressing a finger against the head of a cap provided with a pump mechanism. At the time of use, a mixture of the liquid cleansing composition in the container mixed with air is passed through one or more porous membranes to dispense the liquid cleansing composition from a dispensing mouth of the container in the form of a foam.

The porous membrane of the pump foamer container may, for example, be a sponge, a sintered compact, or a net, of which a net, being thin, is preferable in view of ease of use and the like. As the pore size, one of approximately 30 to 400 mesh should preferably be used. The cleansing composition of the present invention preferably uses a container comprising two porous membranes, and despite combination of 200 and 305 mesh, is capable of providing a good foam quality without causing clogging.

The cleansing composition of the present invention is preferably used as a hair or skin cleanser contained in a pump foamer container, such as a facial cleanser, body soap, hand soap, shampoo or the like.

EXAMPLES

Herebelow, the present invention will be explained in further detail by giving specific examples, but they do not in any way limit the technical scope of the present invention.

In the following examples, the content is in mass% as long as it is not indicated otherwise.

Cleansers were prepared by conventional methods with the compositions described in the examples provided in the below-given table.

The cleansers obtained in the respective examples were evaluated in the following categories according to the below-described criteria.
(1) Low-Temperature Stability Carbon dioxide was forcibly blown into the prepared cleansing compositions, putting them into a state of lowered pH (pH 9.5) caused by passage of time during actual use. This cleansing composition was loaded into hard glass vials, stored for 1 month in evaluation chambers held at respective temperatures (−5 to 20° C.), then the low-temperature stability of the cleansing compositions was observed by eye and graded according to the evaluation criteria described below.
A: good (no precipitation or sedimentation, no change in appearance)
B: acceptable (slight change in appearance (precipitation, sedimentation) but no problems for practical use)
C: defective (precipitation and sedimentation, problems in quality)
(2) Organoleptic Test Cleansers of the respective examples were loaded into pump foamer containers (200×305 mesh), dispensed as foam and actually used by 10 expert panelists, and evaluated in categories such as foaming ability, foam quality and rinsability according to the criteria described below. Each category was divided into the four grades indicated below by the total points awarded by the expert panelists. Those evaluated as AA or A can be considered to have properties adequate for use as a product.
[Evaluation Criteria]
5 points: very good
4 points: good
3 points: fair
2 points: poor
1 point: very poor
[Evaluation Results]
AA: total of 40 points or more
A: total of 30 to 39 points
B: total of 20 to 29 points
C: total of 19 points or less
(3) Clogging The prepared cleansing compositions were loaded into pump foamer containers having a porous membrane of 200×305 mesh and dispensed several times, then dried for 1 week in an incubator at 50° C. Then, they were evaluated as to whether the mesh was clogged or not upon further dispensing (N=5).
[Evaluation Results]
A: Not one instance of clogging out of 5 samples.
C: One or more instances of clogging among 5 samples.

TABLE 1

| Type | Ingredient | Test Example 1 | Test Example 2 | Test Example 3 |
|---|---|---|---|---|
| Water | Ion exchanged water | balance | balance | balance |
| Polyhydric alcohol | Glycerin | 20 | 10 | |
| | Propylene glycol | | 10 | 20 |
| | Dipropylene glycol | 10 | 10 | |
| Ionic surfactant | Myristic acid | 3 | 3 | 3 |
| | Potassium hydroxide | 0.75 | 0.75 | 0.75 |
| | Total | 100 | 100 | 100 |
| | Foam quality | A | A | C |
| | Rinsability | AA | AA | AA |
| Low-temperature stability | 10° C. | C | C | A |
| | 15° C. | C | A | A |
| | 20° C. | C | A | A |

TABLE 2

| Type | Ingredient | Test Example 4 | Test Example 5 | Test Example 6 | Test Example 7 |
|---|---|---|---|---|---|
| Water | Ion exchanged water | balance | balance | balance | balance |
| Polyhydric alcohol | Glycerin | 20 | | | |
| | Polyethylene glycol 400 | | 20 | | |
| | Dipropylene glycol | | | 20 | |
| | Sorbitol | | | | 20 |
| | Propylene glycol | 10 | 10 | 10 | 10 |

TABLE 2-continued

| Type | Ingredient | Test Example 4 | Test Example 5 | Test Example 6 | Test Example 7 |
|---|---|---|---|---|---|
| Ionic surfactant | Laurie acid | 1 | 1 | 1 | 1 |
| | Myristic acid | 1 | 1 | 1 | 1 |
| | Potassium hydroxide | 0.55 | 0.55 | 0.55 | 0.55 |
| | Lauryl betaine | 0.2 | 0.2 | 0.2 | 0.2 |
| Chelating agent | EDTA-2Na 2H$_2$O | 0.02 | 0.02 | 0.02 | 0.02 |
| | Fragrance | 0.1 | 0.1 | 0.1 | 0.1 |
| | Total | 100 | 100 | 100 | 100 |
| | Foam quality | A | A | A | AA |
| | Rinsability | A | A | A | A |
| Low-temperature stability | 5° C. | A | A | A | A |
| | 10° C. | A | A | A | A |
| | 15° C. | A | A | A | A |

The results shown in Table 1 and Table 2 demonstrate that sufficient low-temperature stability cannot be obtained unless propylene glycol is included among the polyhydric alcohols blended into the cleanser. However, when the propylene glycol content exceeded 20 mass % with respect to the entire composition, the problem of reduced foam quality occurred (Table 1).

On the other hand, when the polyhydric alcohol contained 10 mass % of propylene glycol, satisfactory results were obtained for each category, but particularly when sorbitol was added as a polyhydric alcohol, the foam quality further improved, providing a good foam with a doughy texture (Table 2).

amount of propylene glycol, had sufficient foaming ability, excellent foam quality and low-temperature stability, and had good rinsability. In particular, Example 1 containing coconut oil fatty acid diethanolamide exhibited good stability even at low temperatures of 0° C. or below, thus having the property of being well capable of, for example, withstanding wintertime use in cold regions. Additionally, even with Examples 2 and 3 which do not contain coconut oil fatty acid diethanolamide, while a slight change in appearance (of a level presenting no problems for practical use) was observed at −5° C., the stability at 0° C. or higher was good, so the properties were adequate in common use mode. Even when the propylene glycol content was reduced to 5

TABLE 3

| Type | Ingredient | Example 1 | Example 2 | Example 3 | Comparative Example 1 |
|---|---|---|---|---|---|
| Water | Ion exchanged water | balance | balance | balance | balance |
| Polyhydric alcohol | Glycerin | 20 | 20 | 20 | 20 |
| | Propylene glycol | 10 | 10 | 5 | 10 |
| | Dipropylene glycol | 5 | 5 | 5 | 5 |
| | Sorbitol | 10 | 10 | 10 | 10 |
| Ionic surfactant | Lauric acid | 1.8 | 1.8 | 1.8 | 4 |
| | Myristic acid | 0.3 | 0.3 | 0.3 | 1 |
| | Palmitic acid | 0.1 | 0.1 | 0.1 | 0.2 |
| | Potassium hydroxide | 0.65 | 0.65 | 0.65 | 1.5 |
| | Lauryl betaine | 0.2 | 0.2 | 0.2 | 0.2 |
| Non-ionic surfactant | Coconut oil fatty acid diethanolamide (1:1 type) | 0.45 | | | 0.45 |
| Chelating agent | EDTA-3Na 2H$_2$O | 0.02 | 0.02 | 0.02 | 0.02 |
| Preservative | Phenoxyethanol | 0.1 | 0.1 | 0.1 | 0.1 |
| | Fragrance | 0.1 | 0.1 | 0.1 | 0.1 |
| | Total | 100 | 100 | 100 | 100 |
| | Foam quality/foamability | AA | A | A | AA |
| | Rinsability | A | A | A | C |
| | Clogging | A | A | A | A |
| Low-temperature stability | −5° C. | A | B | N/T* | C |
| | 0° C. | A | A | A | C |
| | 5° C. | A | A | A | A |
| | 10° C. | A | A | A | A |
| | 15° C. | A | A | A | A |

*N/T = Not tested

As is clear from the experimental results shown in Table 3, Examples 1-3, wherein the amount of ionic surfactant of which at least 90 mass % was accounted for by a higher fatty acid soap was suppressed to 2 to 5 mass %, and containing 20 to 60 mass % of a polyhydric alcohol including a certain mass % (Example 3), roughly the same properties as for the case of adding 10 mass % of propylene glycol (Example 2) were observed.

In contrast, in Comparative Example 1 wherein the ionic surfactant (higher fatty acid soap) content exceeded 5 mass %, the foaming ability and foam quality were sufficient, but the rinsability was inferior, and the low-temperature stability was also inadequate.

TABLE 4

| Type | Ingredient | Comparative Example 2 | Comparative Example 3 | Comparative Example 4 |
|---|---|---|---|---|
| Water | Ion exchanged water | balance | balance | balance |
| Polyhydric alcohol | Glycerin | 20 | 20 | 5 |
| | Propylene glycol | 10 | 10 | 5 |
| | Dipropylene glycol | 5 | 5 | 5 |
| | Soribtol | 10 | 10 | |
| Ionic surfactant | Lauric acid | 1.55 | 1.55 | 1.8 |
| | Myristic acid | 0.25 | 0.25 | 0.3 |
| | Palmitic acid | 0.1 | 0.1 | 0.1 |
| | Potassium hydroxide | 0.55 | 0.55 | 0.65 |
| | Sodium laureth sulfate | 0.4 | | 0.2 |
| | Lauryl betaine | 0.2 | 0.6 | 0.2 |
| Non-ionic surfactant | Coconut oil fatty acid diethanolarnide (1:1 type) | 0.45 | 0.45 | 0.45 |
| Chelating agent | EDTA-3Na 2H$_2$O | 0.02 | 0.02 | 0.02 |
| Preservative | Phenoxyethanol | 0.1 | 0.1 | 0.1 |
| | Fragrance | 0.1 | 0.1 | 0.1 |
| | Total | 100 | 100 | 100 |
| | Foam quality/foamability | AA | AA | B |
| | Rinsability | B | B | A |
| | Clogging | A | A | C |
| Low-temperature stability | −5° C. | A | A | N/T* |
| | 0° C. | A | A | N/T |
| | 5° C. | A | A | N/T |
| | 10° C. | A | A | N/T |
| | 15° C. | A | A | N/T |

*N/T = Not tested

As is clear from the experimental results of Table 4, in Comparative Examples 2 and 3 in which the proportion occupied by higher fatty acid soaps in the ionic surfactant that was added was less than 90 mass %, the rinsability was inadequate, and in Comparative Example 4 in which the polyhydric alcohol content was less than 20 mass %, clogging occurred in the porous membrane of the pump foamer.

| (Formulation Example 1) | (mass %) |
|---|---|
| Ion exchanged water | balance |
| Glycerin | 15 |
| Propylene glycol | 10 |
| Dipropylene glycol | 5 |
| 1,3-Butylene glycol | 2 |
| Sorbitol | 15 |
| Laurie acid | 1 |
| Myristic acid | 1 |
| Palmitic acid | 0.2 |
| Potassium hydroxide | 0.55 |
| Sodium methyl cocoyl taurate | 0.1 |
| Lauryl betaine | 0.1 |
| Coconut oil fatty acid diethanolamide (1:1 type) | 0.45 |
| EDTA-3Na 2H$_2$O | 0.02 |
| Phenoxyethanol | 0.2 |

What is claimed is:

1. A cleansing composition to be dispensed by a pump foamer, comprising:
   (a) 2 to 5 mass% of at least one ionic surfactant; and
   (b) 20 to 60 mass% of a polyhydric alcohol comprising propylene glycol;
   wherein at least 90 mass% of said ionic surfactant (a) is accounted for by a higher fatty acid soap having 5 to 25 carbon atoms, and the amount of propylene glycol contained in the (b) polyhydric alcohol is less than 20 mass% with respect to the entire composition, and
   wherein at least 92.7 mass% of said ionic surfactant (a) is accounted for by a higher fatty acid soap having 5 to 25 carbon atoms.

2. The composition of claim 1, wherein:
   the polyhydric alcohol further comprises sorbitol.

3. The composition of claim 1, further comprising:
   coconut fatty acid diethanolamide.

4. The composition of claim 2, further comprising:
   coconut fatty acid diethanolamide.

5. A cleansing composition to be dispensed by a pump foamer, comprising:
   (a) 2 to 5 mass% of at least one ionic surfactant; and
   (b) 20 to 60 mass% of a polyhydric alcohol comprising propylene glycol;
   wherein at least 92.2 mass% of said ionic surfactant (a) is accounted for by a higher fatty acid soap having 5 to 25 carbon atoms, and the amount of propylene glycol contained in the (b) polyhydric alcohol is less than 20 mass% with respect to the entire composition.

6. A cleansing composition to be dispensed by a pump foamer, comprising:
   (a) 2 to 5 mass% of at least one ionic surfactant; and
   (b) 20 to 60 mass% of a polyhydric alcohol comprising propylene glycol;
   wherein 92.2 mass% of said ionic surfactant (a) is accounted for by a higher fatty acid soap having 5 to 25 carbon atoms, and the amount of propylene glycol contained in the (b) polyhydric alcohol is less than 20 mass% with respect to the entire composition; and
   a fatty acid diethanolamide.

7. A cleansing composition to be dispensed by a pump foamer, comprising:
   (a) 2 to 5 mass% of at least one ionic surfactant;
   (b) 20 to 60 mass% of a polyhydric alcohol comprising propylene glycol;
   wherein at least 90 mass% of said ionic surfactant (a) is accounted for by a higher fatty acid soap having 5 to 25 carbon atoms, and the amount of propylene glycol contained in the (b) polyhydric alcohol is less than 20 mass% with respect to the entire composition; and
   a fatty acid diethanolamide.

8. The composition of claim 7, wherein:
   the polyhydric alcohol comprises sorbitol.

9. The composition of claim 7, wherein:
   said fatty acid diethanolamide is coconut fatty acid diethanolamide.

* * * * *